United States Patent
Ries

(10) Patent No.: US 10,226,357 B2
(45) Date of Patent: Mar. 12, 2019

(54) INTERBODY CAGE

(71) Applicant: JOIMAX GMBH, Karlsruhe (DE)

(72) Inventor: Wolfgang Ries, Linkenheim (DE)

(73) Assignee: JOIMAX GMBH, Karlsruhe (DE)

( * ) Notice: Subject to any disclaimer, the term of this patent is extended or adjusted under 35 U.S.C. 154(b) by 287 days.

(21) Appl. No.: 14/911,840

(22) PCT Filed: Jun. 25, 2014

(86) PCT No.: PCT/EP2014/001719
§ 371 (c)(1),
(2) Date: Feb. 12, 2016

(87) PCT Pub. No.: WO2015/022039
PCT Pub. Date: Feb. 19, 2015

(65) Prior Publication Data
US 2016/0193055 A1    Jul. 7, 2016

(30) Foreign Application Priority Data

Aug. 14, 2013  (DE) .................... 20 2013 007 341 U
Apr. 25, 2014  (DE) .................... 20 2014 003 441 U

(51) Int. Cl.
*A61F 2/44* (2006.01)
*A61F 2/46* (2006.01)
*A61F 2/30* (2006.01)

(52) U.S. Cl.
CPC ........ *A61F 2/4455* (2013.01); *A61F 2/30771* (2013.01); *A61F 2/442* (2013.01);
(Continued)

(58) Field of Classification Search
CPC ............... A61L 2430/02; A61L 31/146; A61B 17/8625; A61B 17/86; A61F 2/44
(Continued)

(56) References Cited

U.S. PATENT DOCUMENTS

| | | | | |
|---|---|---|---|---|
| 5,674,294 A | * | 10/1997 | Bainville | ............... A61F 2/442 623/17.16 |
| 6,086,613 A | * | 7/2000 | Camino | ................... A61F 2/44 623/17.16 |
| 7,320,708 B1 | * | 1/2008 | Bernstein | .................. A61F 2/44 623/17.15 |
| 8,152,852 B2 | | 4/2012 | Biyani | |
| 8,353,964 B2 | | 1/2013 | Carpenter | |

(Continued)

FOREIGN PATENT DOCUMENTS

| | | |
|---|---|---|
| FR | 2 977 474 A1 | 1/2013 |
| JP | 2002-503135 A | 1/2002 |
| JP | 2003-505199 A | 2/2003 |
| JP | 2012-508048 A | 4/2012 |

(Continued)

OTHER PUBLICATIONS

US 2013/096685 A1. The reference has been cited in the International Search Report under Category X as being relevant to claims 1-3 and 6-11 and under Category Y as being relevant to claims 14-19.

(Continued)

*Primary Examiner* — David W Bates
(74) *Attorney, Agent, or Firm* — McGlew and Tuttle, P.C.

(57) ABSTRACT

An interbody cage, which has lattice-like or grid-like areas for better connection/fusion into the area of the vertebra. The cage has especially an outer frame, which includes massive support parts and, and an inner grid body. The frame determining the outer contour and the lattice or grid areas located within same are made in one piece. The cage is prepared by sintering, such as by electron beam melting or laser sintering.

20 Claims, 4 Drawing Sheets

(52) U.S. Cl.
CPC ............ *A61F 2/447* (2013.01); *A61F 2/4611* (2013.01); *A61F 2002/3093* (2013.01); *A61F 2002/3097* (2013.01); *A61F 2002/30454* (2013.01); *A61F 2002/30523* (2013.01); *A61F 2002/30598* (2013.01); *A61F 2002/30607* (2013.01); *A61F 2002/30777* (2013.01); *A61F 2002/30779* (2013.01); *A61F 2002/30784* (2013.01); *A61F 2002/30785* (2013.01); *A61F 2002/30789* (2013.01); *A61F 2002/30831* (2013.01); *A61F 2002/30843* (2013.01); *A61F 2002/30909* (2013.01); *A61F 2002/30911* (2013.01); *A61F 2002/30912* (2013.01); *A61F 2002/30968* (2013.01); *A61F 2002/30978* (2013.01); *A61F 2002/4475* (2013.01); *A61F 2002/4495* (2013.01); *A61F 2002/4627* (2013.01); *A61F 2310/00023* (2013.01); *A61F 2310/00047* (2013.01)

(58) Field of Classification Search
USPC ............................................ 623/17.11–17.16
See application file for complete search history.

(56) References Cited

U.S. PATENT DOCUMENTS

| | | | |
|---|---|---|---|
| 8,377,136 B2 | 2/2013 | Simonton | |
| 8,663,332 B1* | 3/2014 | To | A61F 2/442 623/17.16 |
| 9,636,226 B2* | 5/2017 | Hunt | A61F 2/447 |
| 9,918,849 B2* | 3/2018 | Morris | A61F 2/30744 |
| 9,949,834 B2* | 4/2018 | Pressacco | A61F 2/30771 |
| 2002/0099444 A1 | 7/2002 | Boyd | A61F 2/28 623/17.16 |
| 2004/0018657 A1 | 9/2004 | Lange et al. | |
| 2005/0112397 A1 | 5/2005 | Rolfe et al. | |
| 2006/0074488 A1* | 4/2006 | Abdou | A61F 2/44 623/17.11 |
| 2007/0116734 A1* | 5/2007 | Akash | A61F 2/30 424/423 |
| 2009/0005870 A1* | 1/2009 | Hawkins | A61F 2/4455 623/17.11 |
| 2009/0138083 A1 | 5/2009 | Biyani | |
| 2009/0192616 A1* | 7/2009 | Zielinski | A61F 2/4425 623/17.16 |
| 2010/0152853 A1 | 6/2010 | Kirschman | |
| 2010/0262248 A1 | 10/2010 | Soumac et al. | |
| 2010/0324682 A1 | 12/2010 | Castro | |
| 2011/0014081 A1 | 1/2011 | Jones et al. | |
| 2011/0172775 A1* | 7/2011 | Flickinger | A61F 2/4465 623/17.16 |
| 2011/0190888 A1* | 8/2011 | Bertele | A61F 2/30907 623/17.11 |
| 2013/0096685 A1 | 4/2013 | Ciupik et al. | |
| 2013/0325129 A1 | 12/2013 | Huang | |
| 2015/0250607 A1* | 9/2015 | Drochner | A61F 2/4455 623/17.16 |

FOREIGN PATENT DOCUMENTS

| | | |
|---|---|---|
| JP | 3184817 U | 7/2013 |
| TW | 201 240 653 A | 10/2012 |
| WO | 2008/033457 A2 | 3/2008 |
| WO | 2013/063194 A1 | 5/2013 |

OTHER PUBLICATIONS

WO 2013/063194 A1. The reference has been cited in the International Search Report under Category Y as being relevant to claims 14-19 and under Category A as being relevant to claim 1. The reference in English is attached.
US 2006/074488 A1. The reference has been cited in the International Search Report under Category X as being relevant to claims 1-3, 5, 7, 9, 11 and 17-19.
TW 201 240 653 A. The reference has been cited in the International Search Report under Category X as being relevant to claims 1-3, 6 and 17. The reference discloses a hollow-grid medical implant. The reference is attached. No English translation is available to Applicant at this time, however attached is an English-language abstract. Applicant also Wishes to disclose the corresponding U.S. patent publication, US 2013325129 A1.
US 2011/014081 A1. The reference has been cited in the International Search Report under Category X as being relevant to claims 1-7, 10-14 and 20.
US 2005/112397 A1. The reference has been cited in the International Search Report under Category X as being relevant to claims 1, 3, 4 and 20.
FR 2 977 474 A1. The reference has been cited in the International Search Report under Category X as being relevant to claim 1. The reference discloses an interbody cage. The reference is attached. No English translation is available to Applicant at this time.
US 2010/152853 A1. The reference has been cited in the International Search Report under Category A as being relevant to claims 1-20.
U.S. Pat. No. 8,353,964 B2. The reference has been cited in the German Search Report under Category X as being relevant to claims 1, 2, 4, 6 and 12.
U.S. Pat No. 8,377,136 B2. The reference has been cited in the German Search Report under Category Y as being relevant to claims 2, 6-8 and 10.
US 2004/0186572 A1. The reference has been cited in the German Search Report under Category Y as being relevant to claims 2, 6-8 and 13.
US 2010/0262248 A1. The reference has been cited in the German Search Report under Category X as being relevant to claims 1 and 9.
US 2010/0324682 A1. The reference has been cited in the German Search Report under Category X.
WO 2008/033457 A2. The reference has been cited in the German Search Report under Category X as being relevant to claims 1, 2, 4, 6, 7 and 9. The reference in English is attached. Applicant also wishes to disclose the corresponding U.S. patent, U.S. Pat. No. 8,152,852 B2, and the corresponding U.S. patent publication, US 2009/0138083 A1.
International Search Report dated Sep. 4, 2014.
German Search Report dated Jan. 9, 2014.
JP 3184817. The reference discloses a textured implant device. The reference is attached. No English translation is available to Applicant at this time, however attached is an English-language abstract.
JP 2002-503135. The reference discloses a spinal spacer that includes a body sized and configured for engagement between adjacent vertebrae. The reference is attached. No English translation is available to Applicant at this time, however attached is an English-language abstract.
JP 2003-505199. The reference discloses a vertebral implant that consists of a frame from cortical osseous material. The reference is attached. No English translation is available to Applicant at this time, however attached is an English-language abstract.
US 2006/0074488, which has been previously disclosed in the Information Disclosure Statement of Feb. 12, 2016.
WO 2013/063194, which has been previously disclosed in the Information Disclosure Statement of Feb. 12, 2016.
JP 2012-508048. The reference discloses an implant for fusing spinal column segments. The reference is attached. No English translation is available to Applicant at this time, however attached is an English-language abstract.

* cited by examiner

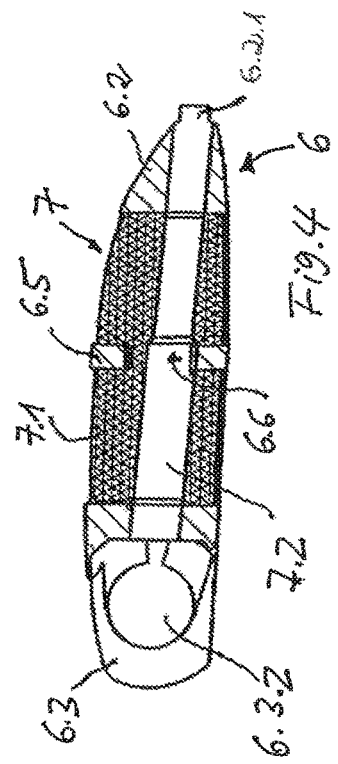
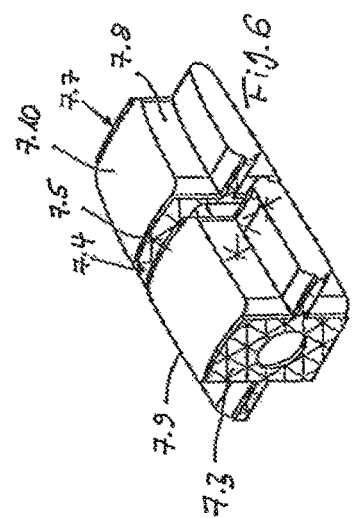
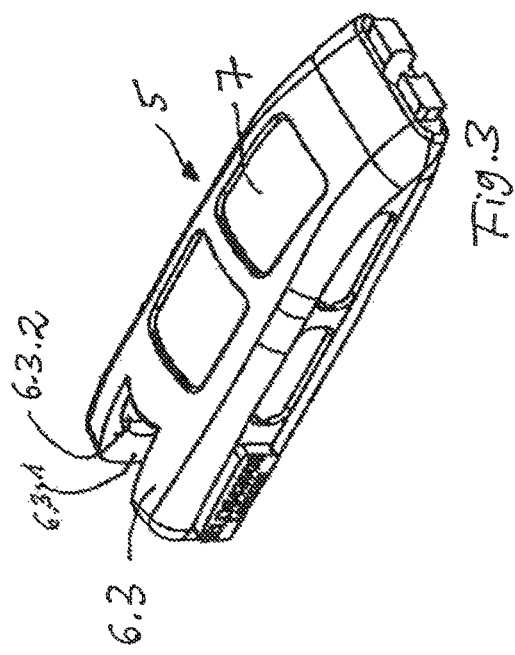
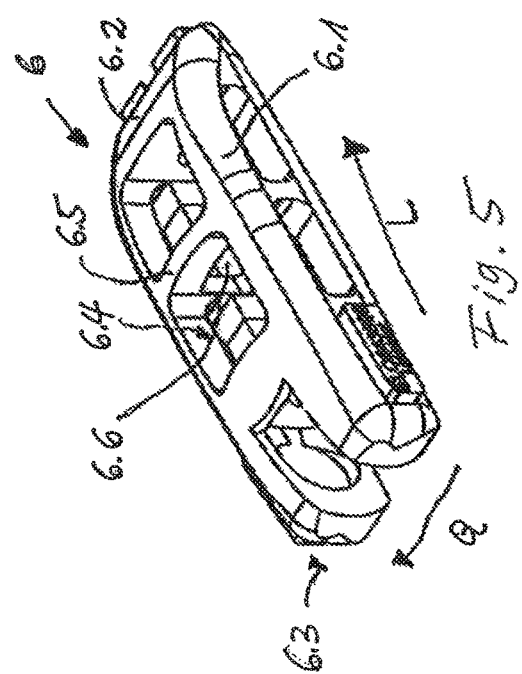

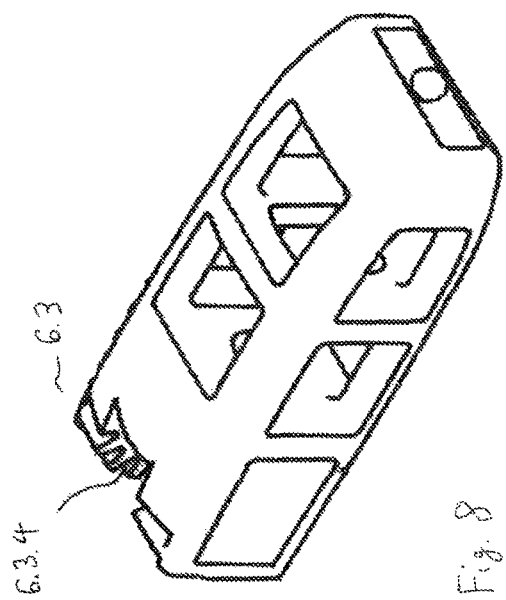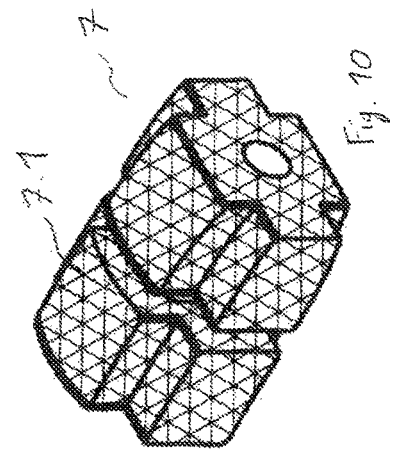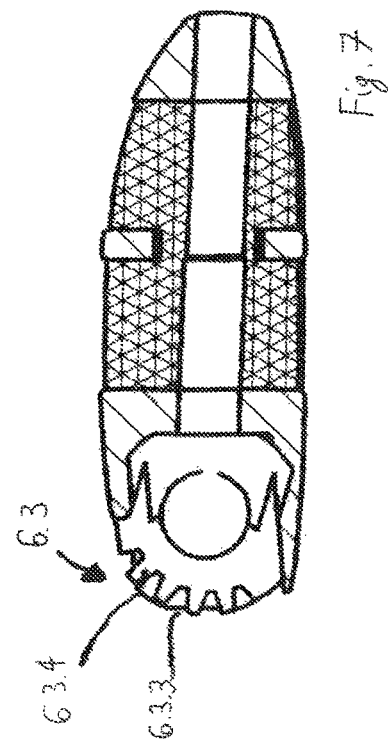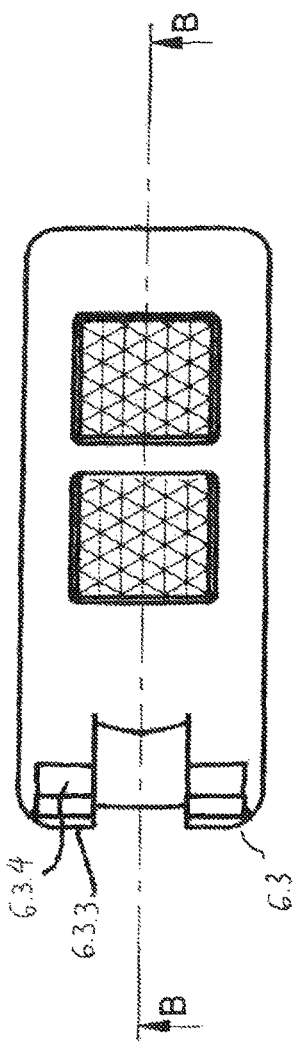

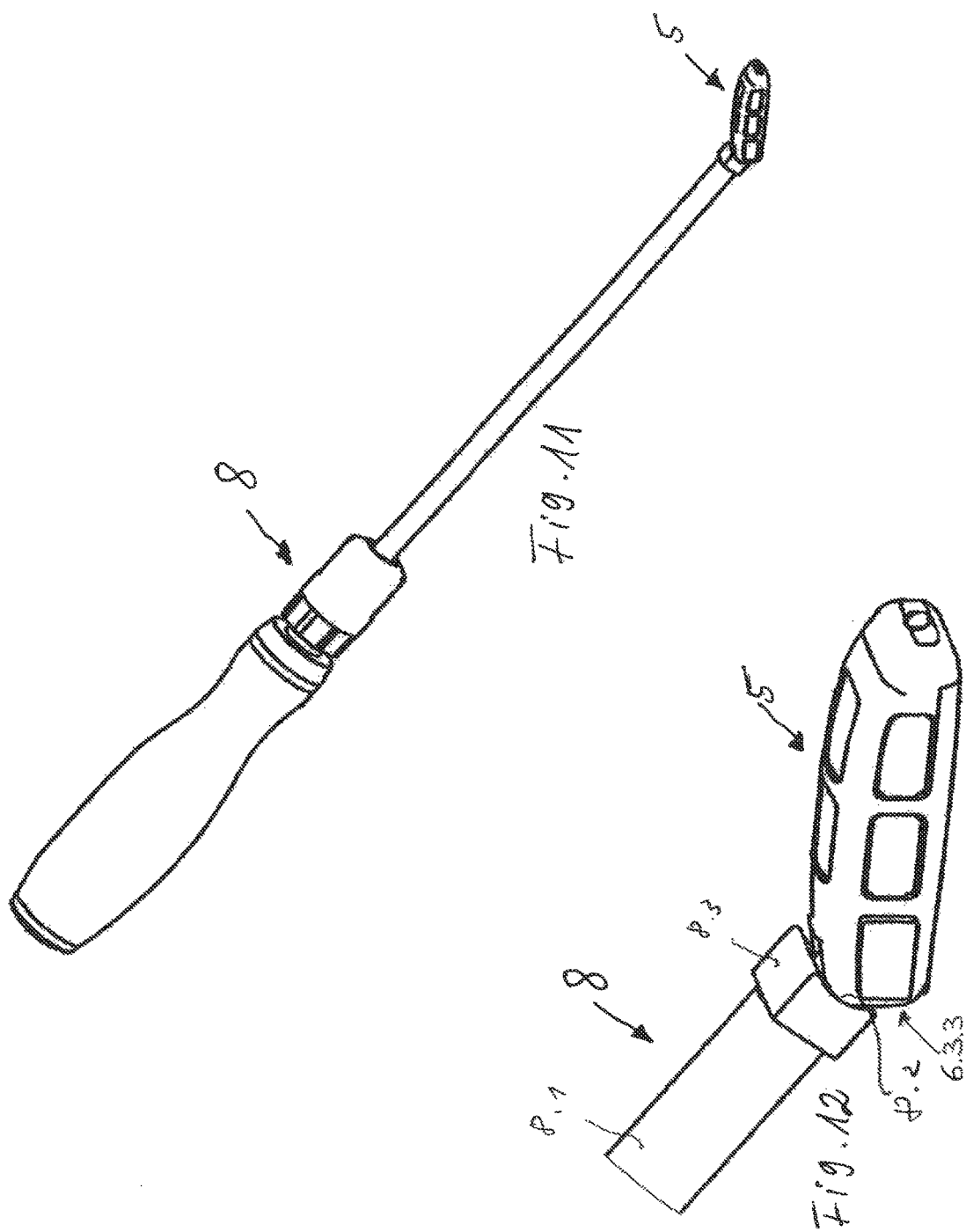

INTERBODY CAGE

CROSS REFERENCE TO RELATED APPLICATIONS

This application is a United States National Phase application of International Application PCT/EP2014/001719 filed Jun. 25, 2014 and claims the benefit of priority under 35 U.S.C. § 119 of German Utility Model Application 20 2013 007 341.1 filed Aug. 14, 2013 and German Utility Model Application 20 2014 003 441.9 filed Apr. 25, 2014, the entire contents of which are incorporated herein by reference.

FIELD OF THE INVENTION

The invention pertains to an interbody cage.

BACKGROUND OF THE INVENTION

Intervertebral cages are called interbody cages in English.

Reinforcement of the spine between the two vertebral bodies affected by a lesion is performed in a number of spinal lesions, especially lesions to intervertebral disks, such as spondylolisthesis and instability following disk herniation, due to stenosis and degeneration. Following removal of an intervertebral disk, which is affected by the lesion and/or causes (nerve) damage, from the intervertebral disk space between two vertebrae of the spine, which are located directly adjacent to one another, cages are inserted for this in order to maintain these vertebrae at the preset distance. The spine is reinforced at least in the area of these two vertebrae. This is called, e.g., lumbar interbody fusion (LIF). The vertebra are optionally also provided, in a minimally invasive spinal procedure, with a screw-rod unit, facet joint screws or translaminar screws and braced against the cage located between them. It is thus also desirable for the bones to fuse with the cage. Such a cage is therefore usually provided with a rough surface.

SUMMARY OF THE INVENTION

An object of the present invention is to provide an interbody cage, which possesses improved properties.

Provisions are made in a preferred embodiment for a frame determining the outer contour and a lattice or grid area located within said frame being made in one piece and being prepared, in particular, by sintering, such as by means of electron beam melting or laser sintering.

This object is accomplished according to the present invention with a cage that has at least areas with a lattice-like or grid-like structure. It is correspondingly formed with lattice-like or grid-like areas.

Such a cage is preferably prepared by sintering, especially by means of (selective) electron beam melting ((S)EBM) or by means of laser sintering (LST). Accordingly, the cage is prepared by sintering, e.g., by means of electron beam melting or laser sintering.

The lattice-like or grid-like areas preferably extend from an upper surface or lateral surface to the parallel lower surface or lateral surface located opposite. It is achieved hereby that bone tissue will grow on the cage not only externally on the surface, but it will also grow into the cavities of the grid-like or lattice-like structure and thus can fully penetrate the cage and bone growth will be promoted. A firm connection is achieved hereby between the cage and the adjacent vertebral body.

The cages may preferably have a length of 22 mm to 40 mm and a width on the order of magnitude of between 10 mm and 15 mm and a different height ranging from 6 mm to 16 mm depending on the patient's constitution and the site of insertion and the vertebral bodies and the intervertebral space thereof, into which the cage shall be inserted. With these widths and heights, the cages can be inserted into the intervertebral space between the vertebral bodies through a working sleeve.

Provisions are made in a preferred variant for the cage to be provided with an outer frame, which comprises massive carrying parts, and with an inner grid body. Due to the cage being designed with two structural elements, namely, an—outer—frame consisting of a compact material and having a compact structure and an inner grid body with said lattice-like or grid-like structure, sufficient strength and rigidity is imparted to the cage, while the aforementioned advantages in terms of complete infiltration of bone material through the cage and the grid-like structure thereof are preserved.

Provisions are made in another, extremely preferred embodiment of the present invention for the grid body to be connected to the frame on parallel surfaces extending in one direction (transverse direction) only, but not to be in connection with the frame in surfaces and edges extending at a finite angle in relation to those surfaces. An uncoupling of the outer frame and the grid body of the cage is achieved hereby in a certain way by the two being uncoupled in the longitudinal direction or the main direction in which the cage extends (the cage is longer in the insertion direction than in the transverse direction and in its height). When the frame yields, for example, in the area of ribs forming it under pressure being exerted on it, this pressure is not transmitted to the grid body. The latter thus remains uncompromised and even bone structure growing into it is not compromised or damaged.

Provisions are made in a preferred variant for the upper and lower surfaces of the grid body to have the same dimensions as free spaces that are surrounded by frame components and surround said surfaces of the grid body.

Provisions are made in another embodiment of the cage according to the present invention for the frame to surround a cavity, in which the grid body is arranged. Provisions are made in a variant for the frame to have longitudinal ribs extending in its longitudinal direction. Provisions are made in an extremely preferred embodiment for adjacent longitudinal ribs to be connected in the center by cross ribs. The stability of the frame and hence of the cage itself is increased hereby even in case of longer cages. The lattice or grid structure of the grid body of the cage may have various designs. Provisions are made in an extremely preferred embodiment for the grid area or grid body to have a diamond structure.

Provisions may be made in another embodiment of the cage for the cage having a through passage. The perforation extends in the longitudinal direction through the frame and especially also through the grid body itself. It is achieved hereby that the cage can be inserted through a tubular lock or an endoscope tube via a guide wire extending into the intervertebral disk space.

Further preferred embodiments of the cage according to the present invention are characterized in that the grid-like areas or the grid body have grid opening diameters of each opening ranging from 0.5 mm to 3.5 mm, the opening diameters of each opening being on the order of magnitude of 0.5 mm to 0.7 mm preferably on the outer side of the cage and/or the grid-like areas or the grid body in the interior of the cage having openings or perforations with diameters of 0.5 mm to 3.5 mm, especially through a proximal connection area for connecting the cage to an insertion instrument.

As was mentioned, a cage can be prepared, especially by (selective) electron beam melting ((S)EBM) or laser sintering technique (LST), from a titanium alloy, especially Ti6Al4V according to ISO 5832-3. The component—cage— is prepared by melting metal powder by means of an electron beam or laser beam under high vacuum. Undercuts can be prepared hereby without lost forms or cores. The metal powder can be melted in a specific manner by an electron beam or laser beam as the energy source, as a result of which compact components of nearly any desired geometry can be prepared directly based on design data. A powder layer is alternatingly applied by means of a blade to the previously applied layer and exposed to the electron beam. The desired component is generated in this way layer by layer.

Provisions are made in a preferred embodiment for a proximal end face to have a tooth. The tooth may also be present as one tooth or more than one tooth. The rest of the design of the tooth may be coordinated with the insertion instrument. Different angular orientations are made possible hereby between the cage and the insertion instrument and it becomes possible to optimally position the cage.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a perspective view of a first embodiment of a cage according to the present invention;

FIG. 4 is a longitudinal sectional view of the cage according to FIG. 3;

FIG. 5 is a perspective view of the frame part of the cage according to FIGS. 3 and 4;

FIG. 6 is a perspective view of the grid body of the cage according to FIGS. 3 and 4;

FIG. 7 is a longitudinal sectional view through another embodiment of the cage according to the present invention;

FIG. 8 is a perspective view of the outer frame of the cage according to the present invention according to FIG. 7;

FIG. 9 is a top view of the cage according to the present invention according to FIGS. 7 and 8;

FIG. 10 is a perspective view of the grid body of the cage according to FIGS. 7-9;

FIG. 11 is a perspective view of a cage according to the present invention with an insertion instrument; and FIG. 12 is an enlarged view of the cage at the distal area of the insertion instrument according to FIG. 11.

DESCRIPTION OF THE PREFERRED EMBODIMENTS

Figure 1:
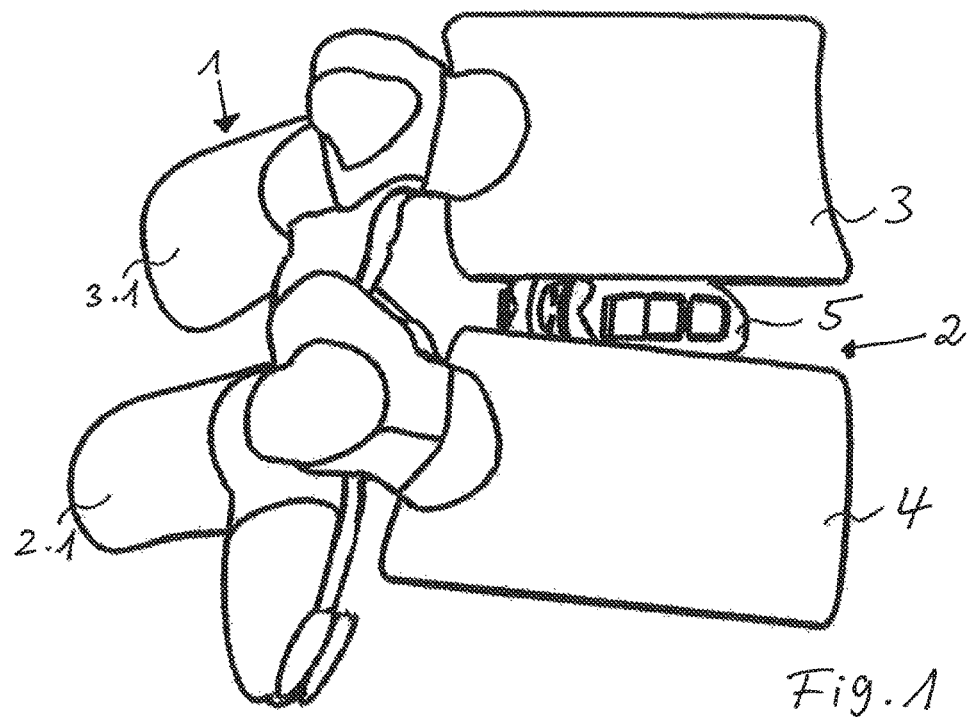
FIG. 1 is a side view of two vertebrae with an interbody cage inserted between them.
Figure 2:
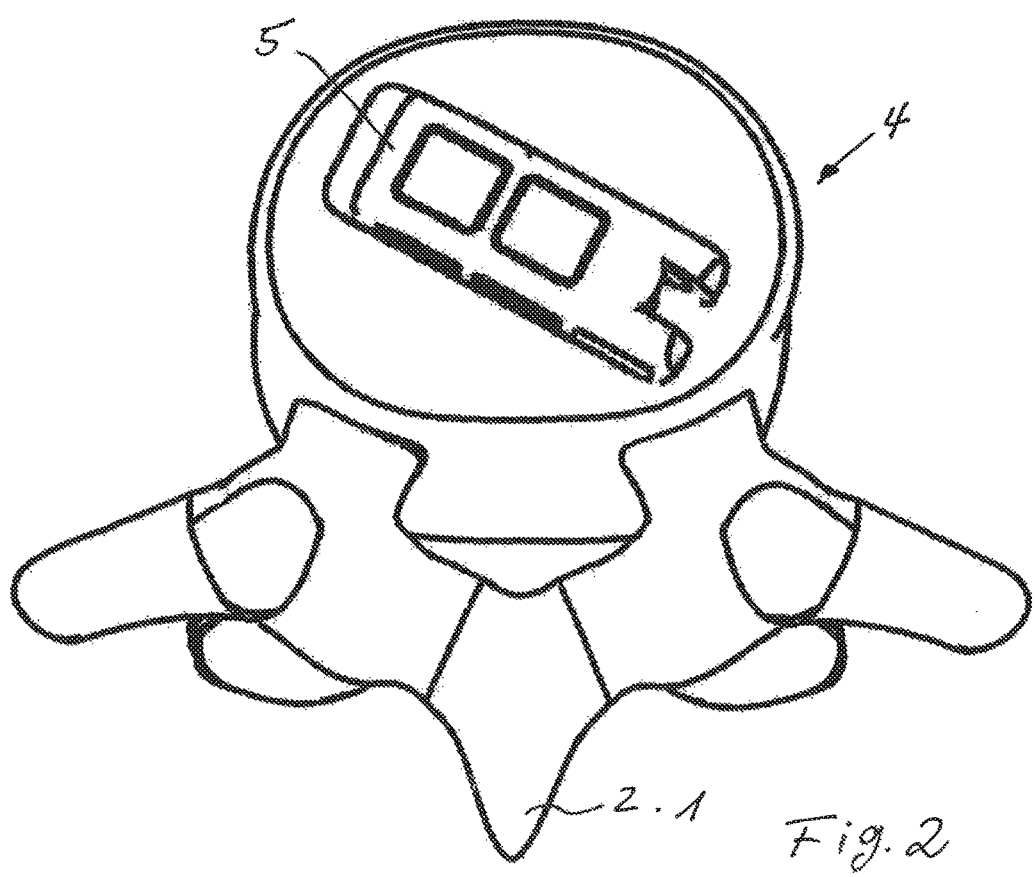
FIG. 2 is a perspective top view of a vertebra with a cage seated on same.

When the intervertebral disk is to be removed from the intervertebral space 2 between two vertebrae 3, 4 of a spine 1, which vertebrae are located one above the other, because of lesion to an intervertebral disk in the spine of a patient, a cage is inserted, instead, in order to keep the vertebrae at a suitable distance, as this is shown in FIGS. 1 and 2. This is, as a rule, accompanied by a reinforcement of the spine in this area, so that the two vertebrae 3, 4, between which the cage 5 is inserted, are no longer movable in relation to one another. Bracing may additionally be performed by means of a screw-rod unit, facet joint screws or translaminar screws. Furthermore, it is desirable for the cage 5 to fuse with the vertebrae and is designed accordingly.

The cage 5 may be inserted in different directions to the processus spinosi 2.1, 3.1, as an oblique cage (O-cage) with an angular orientation of about 6° to the processus spinosi in the exemplary embodiment being shown. Posterior cages (P-cages) are shorter than O-cages and have a length of 24 mm to 30 mm, depending on the patient. They are inserted into the intervertebral space dorsally next to the processus spinosus slightly obliquely in relation to this.

The height of the cage 5 must be adapted to the— original—height of the intervertebral space 2, which may differ from person to person. Therefore, cages 5 with different heights are to be provided depending on the patient's constitution. FIG. 6 shows a cage with a height of 8 mm, and FIGS. 7 through 8 show a cage with a height of 14 mm. Cages with mm increments are usually provided.

In the figures showing the preferred embodiment shown, the cage according to the present invention comprises, in principle, two main components, namely, an—outer—massive frame and an—inner—grid body 7. The grid body 7 has a grid structure, preferably a diamond grid structure with thin ribs 7.1 and with free intermediate spaces between these, the dimensions of the ribs 7.1, especially the thickness thereof (in a direction at right angles to the direction in which the ribs extend between two nodal points, at which they are each connected to additional ribs of the grid) being small compared to all dimensions of structural components of the frame 6, for example, a width of ribs of the frame 6. The size ratios are at least 1 to 10. This correspondingly also applies to the length of struts 7.1 of the grid body 7 between two nodal points and to longitudinal dimensions of structural parts of the frame 6, such as said ribs, so that the ratio is at least 1 to 10 here as well.

The cage 5 is nevertheless a one-piece cage even if it comprises two main components, the frame 6 and the grid body 7.

The frame 6 has four longitudinal ribs 6.1, which connect a distal end area 6.2 of the cage 5 and a proximal connection area 6.3 and enclose a cavity 6.4 with this, in which the grid body is located in the finished cage. The ribs 6.1 are connected to one another by cross ribs 6.5 in the center, i.e., at about half of their length, the connected ribs being always adjacent ribs 6.1. A passage 6.6 will accordingly remain between the cross ribs 6.5. Corresponding passages 6.2.1 and 6.3.1 are also located in the distal end area 6.2 and in the proximal connection area 6.3. Moreover, the grid body 7 is also provided with a longitudinal passage 7.2, which is flush with the aforementioned passages.

In an extremely preferred embodiment, the grid body 7 and the frame 6 are connected to one another—in one piece—only in (surface) areas extending at right angles to the longitudinal direction L and hence on transversely extending (surface) areas, and they are connected only with the surfaces 7.3, 7.4, 7.5, 7.7 (FIGS. 6 and 10).

By contrast, longitudinal surfaces, such as 7.8 and also longitudinal edges, such as 7.9 of the grid body 7, are not rigidly connected to the frame 6. In addition, especially the dimensions of the upper surfaces 7.10 and of the lower surfaces, which are located opposite and in parallel to these on the underside of the grid bodies 7, correspond to the recesses or the areas left free by the longitudinal ribs 6.1, the cross ribs 6.5 and the end face areas 6.2 as well as the proximal connection area 6.3. This causes that when pressure load acts on the longitudinal ribs 6.1 through the vertebral bodies 2, 3, this load is not transmitted on the long sides to the grid body 7 and this thus remains undeformed and can assume its task of guaranteeing the integration of bone material into these honeycombs or intermediate spaces of the grid body 6 even under these circumstances. The continuous longitudinal passage of the cage 5 makes it possible for this cage to be able to be inserted into the intervertebral space via an indwelling guide wire.

In the embodiment of a cage 5 according to the present invention according to FIGS. 7 through 10, the proximal connection area 6.3 of said cage has (at the frame 6) teeth 6.3.4 on its proximally directed outer end face 6.3.3. These [teeth] are used to secure a preset angular orientation between the insertion instrument 8 and the cage 5 during the fixation of the cage 5 at the distal end of an insertion instrument 8 (FIG. 12) by an axial bracing between a hammer-like locking member of the insertion instrument and an abutment 8.3 thereof. The teeth 6.3.4 are formed by the teeth following each other downwardly on a circular arc. There is one tooth 6.3.4 on each side of the proximal passage 6.2.1 of the cage.

The design (e.g., number, distance, shape) of the teeth 6.3.4 may be coordinated with the insertion instrument 8 and/or the meshing. This makes possible, on the one hand, optimal compatibility with the insertion instrument 8 and increased stability of the connection between the abutment 8.3 of the insertion instrument 5 and, on the other hand, a great variety of connection angles.

The insertion of a cage 5 according to the present invention is carried out by means of an insertion instrument 8, as this is shown in FIGS. 11 and 12. A locking element formed by an outer tube 8.1 has a hammer-like locking part rotatable about its longitudinal axis (neither of them being shown), which said locking part is inserted in a vertical orientation into the passage 6.3.1 of the proximal connection area 6.3 of the cage 5, for example, in the view of the cage 5 shown in FIGS. 3 through 5. On its proximal end face, the cage 5 has an undercut opening for this, whose opening cross section corresponds to the locking element of the insertion instrument 8; the undercut opening forms a locking element on the cage 5, which makes it possible to lock the insertion instrument 8 and the cage 5.

The hammer-like locking part of the insertion instrument is then pivoted by 90° relative to the outer tube 8.1, so that it will mesh with undercuts 6.3.2 on the inner side of the wall of the proximal connection area 6.3. The hammer-like locking part and concavely bent front edges 8.2 are braced against one another by means of clamping devices at the proximal end of the insertion instrument 8 at an abutment 8.3 provided distally at the outer tube 8.1 via the intermediary of the proximal connection area 6.3 of the cage 5, wherein the locking part extends behind said proximal connection area 6.3 of the cage 5. The cage 5 is held firmly at the insertion instrument hereby. This makes it possible for the cage 5 to move in the direction in which it extends and with a component in relation to the direction in which the insertion instrument 8 extends. If the proximal connection area 6.3 of the cage 5 has a tooth 6.3.4 on its (outer) end face 6.3.3, this also secures an assumed angular position between the insertion instrument 8 and the cage 5. Nevertheless, pivoting between the insertion instrument 8 and the cage 5 in the vertical direction to the longitudinal extension L of both about a considerable angle of up to 30° and more is possible, as is shown especially in the view of the design of the recess 6.3.2 having a circular shape according to FIG. 4.

While specific embodiments of the invention have been shown and described in detail to illustrate the application of the principles of the invention, it will be understood that the invention may be embodied otherwise without departing from such principles.

The invention claimed is:

1. An interbody cage comprising:
an outer frame determining an outer contour and an inner lattice-like or grid-like area, the outer frame surrounding a cavity, the lattice-like or grid-like area located within the outer frame being an inner grid body, the inner grid body being arranged in the cavity of the outer frame, the inner grid body having a grid structure with ribs and hollow intermediate spaces between the ribs, wherein dimensions of the ribs are less than dimensions of structural components of the outer frame, the outer frame and the grid body being one piece, the inner grid body being connected to the outer frame only on inner grid body surfaces extending parallel to one direction of the outer frame, the grid body not being connected with the outer frame at surfaces and edges at a finite angle relative to the one direction.

2. An interbody cage in accordance with claim 1, wherein the interbody cage is prepared by sintering, said sintering comprising electron beam melting or laser sintering.

3. An interbody cage in accordance with claim 1, wherein upper and lower surfaces of the grid body have same dimensions as free spaces that are surrounded by frame ribs of the outer frame and the frame ribs surround said upper and lower surfaces of the grid body.

4. An interbody cage in accordance with claim 1, wherein the frame has longitudinal frame ribs extending in a longitudinal direction of the frame.

5. An interbody cage in accordance with claim 4, wherein adjacent longitudinal frame ribs are connected in a center by cross ribs.

6. An interbody cage in accordance with claim 1, wherein the grid body has a diamond structure.

7. An interbody cage in accordance with claim 1, further comprising a continuous passage.

8. An interbody cage in accordance with claim 1, wherein the grid-like areas or a grid body have grid opening diameters of each opening ranging from 0.5 mm to 3.2 mm.

9. An interbody cage in accordance with claim 1, wherein the grid-like areas or a grid body have openings or perforations with diameters of 0.5 mm to 3.2 mm in an interior of the cage.

10. An interbody cage in accordance with claim 1, further comprising a proximal connection area for connecting the cage with an insertion instrument.

11. An interbody cage in accordance with claim 10, wherein on an inner side of side walls of the cage, the proximal connection area has depressions, for an angularly movable, undercutting connection with the insertion instrument.

12. An interbody cage in accordance with claim 10, wherein a connection area in an upper side of the cage has a cutout, for angular movement between the cage and the insertion instrument.

13. An interbody cage in accordance with claim 1, further comprising a proximal end face, said proximal end face having a toothing.

14. An interbody cage in accordance with claim 13, wherein the toothing is formed through teeth following each other in a vertical direction on circular segments.

15. An interlocking cage in accordance with claim 13, wherein the toothing is arranged on both sides of a proximal passage formed in a center on the proximal end face.

16. An interbody cage comprising:
an outer frame;
an inner grid body comprising a grid structure having inner grid body surfaces, the inner grid body surfaces extending parallel to one direction of the outer frame, the grid structure comprising grid structure ribs, the grid structure ribs defining a plurality of intermediate spaces, the inner grid body being integrally connected to the outer frame to define a one-piece interbody cage structure, the outer frame defining an interior cavity, the inner grid body being located in the interior cavity, the outer frame defining an outer contour of the one-piece interbody cage structure, wherein dimensions of each of the grid structure ribs are less than dimensions of each part of the outer frame, the inner grid body being connected to the outer frame only on the inner grid body surfaces, the grid body not being connected with the outer frame at surfaces and edges at a finite angle relative to the one direction.

17. An interbody cage in accordance with claim 16, wherein upper and lower surfaces of the inner grid body have same dimensions as free spaces that are surrounded by frame ribs of the outer frame and the frame ribs surround said upper and lower surfaces of the grid body.

18. An interbody cage in accordance with claim 16, wherein the frame has longitudinal frame ribs extending in a longitudinal direction of the frame.

19. An interbody cage in accordance with claim 18, wherein adjacent longitudinal frame ribs are connected in a center by cross ribs.

20. An interbody cage comprising:
an outer frame comprising an upper opening and a lower opening;
an inner grid body comprising a grid structure having inner grid body surfaces, the inner grid body surfaces extending parallel to one direction of the outer frame, the grid structure comprising grid structure ribs, the grid structure ribs defining a plurality of intermediate spaces, the inner grid body being integrally connected to the outer frame to define a one-piece interbody cage structure, the outer frame defining an interior cavity, at least a portion of the inner grid body being arranged in the interior cavity, the outer frame defining at least a portion of an outer contour of the one-piece interbody cage structure, at least a portion of the inner grid body being arranged in the upper opening, at least another portion of the inner grid body being arranged in the lower opening, wherein the inner grid body defines at least another portion of the outer contour of the one-piece interbody cage structure, wherein dimensions of each of the grid structure ribs are less than dimensions of each part of the outer frame, the inner grid body being connected to the outer frame only on the inner grid body surfaces, the grid body not being connected with the outer frame at surfaces and edges at a finite angle relative to the one direction.

* * * * *